United States Patent
Melrose et al.

(12) 
(10) Patent No.: US 6,803,356 B1
(45) Date of Patent: Oct. 12, 2004

(54) ANTIMICROBIAL POLYMERIC COMPOSITIONS

(75) Inventors: Graham John Hamilton Melrose, Dalkeith (AU); Gerry Daly, Gooseberry Hill (AU); Andrew James Huxham, Balga (AU)

(73) Assignee: Chemeq Ltd., Bentley (AU)

( * ) Notice: Subject to any disclaimer, the term of this patent is extended or adjusted under 35 U.S.C. 154(b) by 0 days.

(21) Appl. No.: 10/009,139

(22) PCT Filed: Feb. 16, 2000

(86) PCT No.: PCT/AU00/00107

§ 371 (c)(1),
(2), (4) Date: Nov. 8, 2001

(87) PCT Pub. No.: WO01/60874

PCT Pub. Date: Aug. 23, 2001

(51) Int. Cl.[7] .............................. C11D 3/37; C11D 3/48; C08L 29/00; C08F 16/34; A61K 31/765
(52) U.S. Cl. ...................... 510/475; 568/420; 568/421; 568/449; 526/315; 424/78.08; 424/78.37; 422/36; 514/703
(58) Field of Search ......................... 510/475; 568/420, 568/421, 449; 526/315; 424/78.08, 78.37; 422/36; 514/703

(56) References Cited

U.S. PATENT DOCUMENTS

| 4,479,820 | A |   | 10/1984 | Merk et al. |
| 4,724,142 | A |   | 2/1988 | Mahn et al. |
| 4,724,143 | A |   | 2/1988 | Mahn et al. |
| 5,290,894 | A |   | 3/1994 | Melrose et al. |
| 5,917,094 | A | * | 6/1999 | Werle et al. ............... 568/449 |
| 6,410,040 | B1 | * | 6/2002 | Melrose et al. ............ 424/404 |

FOREIGN PATENT DOCUMENTS

| AU | 11686/95 | * | 8/1995 | .......... C08F/116/34 |
| AU | 711548 | * | 8/1997 | ............. C08G/4/00 |
| AU | 14844/97 |   | 8/1997 | |
| GB | 1509154 |   | 4/1978 | |
| WO | WO 96/38186 | * | 12/1996 | .......... A61K/31/765 |
| WO | WO 00/03723 |   | 1/2000 | |

* cited by examiner

*Primary Examiner*—Brian P. Mruk
(74) *Attorney, Agent, or Firm*—Nixon Peabody LLP

(57) ABSTRACT

A method for the preparation of polymers derived from acrolein and including poly(2-propenal, 2-propenoic acid), characterised in that the polymers are exposed to the presence of water, whereby such polymers exhibit increased antimicrobial activity. The polymers may be heated in the range of 40 to 150° C. Further, the polymers may be prepared in the presence of polyethylene glycols, polyols and/or alkanols.

19 Claims, No Drawings

ANTIMICROBIAL POLYMERIC COMPOSITIONS

FIELD OF THE INVENTION

The present invention relates to antimicrobial polymeric compositions. More particularly, the antimicrobial polymeric compositions of the present invention contain compounds having a polyacrolein sub-unit with its aldehyde group in its free, hydrated, hemi-acetal or acetal form, and having biostatic and/or biocidal properties. The invention is directed to compositions containing these polymeric compounds and the biostatic and/or biocidal uses of these compositions.

BACKGROUND ART

The broad-based antimicrobial properties of polymers (hereinafter called the "subject polymers") having the repeating polymeric unit:

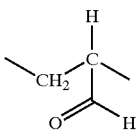

or this unit in its hydrated, hemi-acetal or acetal form, represented by the formulae:

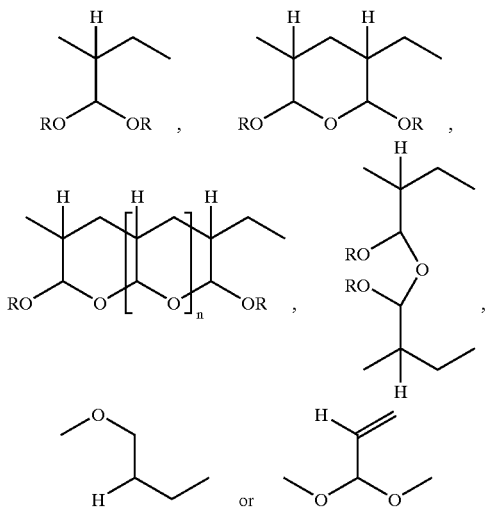

wherein R is hydrogen or alkyl and n is an integer of one or more, have been demonstrated previously (Melrose et al., International Patent Publication WO 88/04671). The subject polymers described therein include poly(2-propenal, 2-propenoic acid).

It has also been noted previously (Melrose, International Patent Publication WO 96/38186) that poly(2-propenal, 2-propenoic acid) is formed when the aldehyde groups of poly(2-propenal) syn polyacrolein are partially auto-oxidised to carboxyl groups, by heating the dry polymer in air, to 100° C. and preferably to between 80° C. and 100° C. It was further noted that the resulting polymer is soluble in dilute aqueous bases, for example aqueous sodium carbonate.

An earlier disclosure (Werle et al., Australian Patent Application 11686/95, now lapsed) claimed solubility of the subject polymers in polyols—but not solubility in aqueous media, following heating to 75° C. It was further claimed that subsequent to the heating to 75° C., brief treatment with sodium hydroxide gave rise to aqueous solubility and apparently as a result, increased antimicrobial activity.

To increase the stability of compositions containing the subject polymers, Melrose & Huxham (International Patent Application PCT/AU99/00578) have formulated compositions with anionic surfactants. Additionally, this prior art revealed that in basic compositions, in contrast to acidic compositions, the subject polymers have faster antimicrobial activity, but are less stable.

It is particularly desirable that the subject polymers should not be unstable, yielding acrolein, as this monomer is very irritating to the eyes, lungs, tissues and skin.

It is one object of the present invention to provide methods of preparing compositions, these methods producing a new configuration of the subject polymers and in particular of poly(2-propenal, 2-propenoic acid), and which have enhanced antimicrobial activity.

It is a further object of the present invention to provide methods of preparing compositions, these methods producing a new configuration of the subject polymers and in particular of poly(2-propenal, 2-propenoic acid), and which better retain antimicrobial activity.

It is a still further object of the present invention to provide methods of preparing compositions, these methods producing a new configuration of the subject polymers and in particular of poly(2-propenal, 2-propenoic acid), and which contain less free acrolein.

It is a yet still further object of the present invention to provide compositions containing a new configuration of the subject polymers and in particular of poly(2-propenal, 2-propenoic acid) which are efficacious disinfectants or antiseptics.

Throughout the specification, unless the context requires otherwise, the word "comprise" or variations such as "comprises" or "comprising", will be understood to imply the inclusion of a stated integer or group of integers but not the exclusion of any other integer or group of integers.

DISCLOSURE OF THE INVENTION

In accordance with the present invention there is provided a method for improving the antimicrobial activity of a polymer derived from acrolein monomer wherein the polymer has been oxidized in air to form an oxidised acrolein polymer comprising carboxyl groups, said method comprising:

providing a solution of the oxidized acrolein polymer comprising carboxyl groups in a mixture containing water and a hydroxylic solvent including an alcohol selected from the group consisting of polyols, polyethylene glycols and alkanols; and heating the solution at a temperature in the range of from 40 to 150° C. for a period sufficient to improve the antimicrobial activity of the acrolein polymer.

Still preferably, the polymers are heated in the range of 40 to 115° C.

Still further preferably, the polymers are heated in the range of 70–90° C.

Preferably, the polymers are heated for a period of between 1 to 1,400 hours, thereby increasing antimicrobial activity of the polymers.

Still preferably, the polymers are heated for a period of between 10 to 60 hours.

In one form of the invention the polymers are heated in the presence of one or more of polyethylene glycol, polyol or alkanol, thereby providing one or both of enhanced stability or enhanced anti microbial activity. Water is invariably present in these alcohols.

Preferably, polyethylene glycol is present during the preparation of the polymers in the amount of between 50 and 99% by weight.

Still preferably, poly ethylene glycol is present during preparation of the polymers in the amount of between 64 and 95% by weight.

In a further form of the invention, base or alkali is added to the polymers before and/or during heating, thereby enhancing the antimicrobial activity of the polymers.

Preferably, the addition of the base or alkali brings the pH of the polymers to between 7 and 9.

Still preferably, the pH is about 8. Sodium hydroxide may be the base added.

In a still further form of the invention, the release of free acrolein monomer is inhibited, thereby the polymers are less likely to present a source of tissue or dermal irritation.

Preferably, the polymer is initially heated, predominantly in the dry state, to between 80 and 100° C.

Still preferably, the polymer is initially heated to about 85° C.

In accordance with the present invention there is further provided an antimicrobial compound or composition prepared by one or more of the methods described hereinabove.

In accordance with the present invention there is still further provided a preservative compound or composition prepared by one or more of the methods described hereinabove.

In accordance with the present invention there is yet still further provided a disinfectant or antiseptic compound or composition prepared wholly or in part by the methods described hereinabove.

Preferably, the disinfectant or antiseptic compound or composition has a pH greater than 6, thereby enhancing antimicrobial activity.

In accordance with the present invention, there are provided methods for the preparation of a new configuration of the subject polymers including poly(2-propenal, 2-propenoic acid) and of compositions therefrom, whereby the compositions exhibit increased antimicrobial activity, and/or increased stability and/or contain less free acrolein, thus making the polymers and/or their compositions more suitable as preservatives, and/or active ingredients in disinfectants and/or, antiseptics, under acidic or basic conditions.

BEST MODE(S) FOR CARRYING OUT THE INVENTION

Since the prior art recorded some instability of poly(2-propenal, 2-propenoic acid), as evidenced by loss of antimicrobial activity of its compositions, the routine procedure in industry was then followed in our laboratories, of quantitatively determining this instability by standard "accelerated ageing" at elevated temperature, ie. at 40° C. However, to our greatest surprise, the elevated temperature of "ageing" poly(2-propenal, 2-propenoic acid) in aqueous or in aqueous-polyethylene glycol solutions at 40° C., not only slowed the decrease in antimicrobial activity—but in fact, actually increased antimicrobial activity of the poly(2-propenal, 2-propenoic acid), see Example 2(a) and (b). This finding is totally contradictory and unexpected in view of the prior art which predicts that the rise in temperature should lead to "accelerated ageing", ie. accelerated loss of antimicrobial activity.

Henceforth, the process of providing increased antimicrobiological activity by the formation of a new configuration of the subject polymers including poly(2-propenal, 2-propenoic acid), is referred to as "super-activation" and the polymers referred to as "super-activated polymers".

Even more surprising, in view of prior art, the inventors have found super-activation in aqueous polyethylene glycol solution is promoted by basic conditions, see Example 2(c).

Also, super-activation is promoted by heat and moisture, alone, see Example 4.

Additionally, it has been found that prior, dry heating of the subject polymers between 80–65° C. gives polymers, see Example 1, which are soluble in aqueous media and suitable for subsequent super-activation.

Super-activation is facilitated by the presence of polyethylene glycols or polyols or alkanols see Example 3, —we believe, since the presence of the polyethylene glycol or polyol or alkanol protects and stabilises the carbonyl groups of the polymers, possibly by formation of acetals, from alkaline degradation by the Cannizarro reaction.

An added advantage of super-activation is that it gives rise to less, contaminant acrolein which is a source of tissue and dermal irritation, see Example 6.

It is emphasised that super-activation is quite distinct and additional to any increase of antimicrobial activity which may result, merely from more polymer being available in any aqueous test-medium as the result of increased hydrophillicity of the polymer such as was demonstrated in lapsed Australian Patent Application AU-A-11686/95 (hereinafter "11686/95"). The inventors have repeated exactly the method described in 11686/95 and then, following, found that subsequent super-activation of the partially soluble polymer demonstratively gave rise to additional, substantial antimicrobial activity, see Example 5. It should be noted that even super-activation did not render the polymer from 11686/95 completely soluble—in contrast to super-activation beginning with polymer firstly heated between to 80–85° C.

The optimum time to achieve super-activation of solutions of poly(2-propenal, 2-propenoic acid) depends inversely upon the temperature, see Example 7. It will be apparent that even ageing at room temperature may be used for super-activation, especially when facilitated in the presence of hydroxylic solvent and/or base, but obviously, this may be impractical due to the longer time periods required.

The inventors have found polymers super-activated as described herein, suitable for preservatives in water-based products or processes, and as well, as active ingredients in disinfectants or antiseptics having the advantage of enhanced antimicrobial activity, see Example 8. Furthermore, the inventors found that the antimicrobial activity of such disinfectants or antiseptics was increased by increase in their pH, for example above pH 6, see again Example 8.

The invention will now be described with reference to several Examples, which should not be construed as limiting the scope thereof.

Biocidal Test

Dilute sample with 1% aqueous sodium bicarbonate to obtain the required concentration (unless specified to the contrary, 0.125% in polymer). Weight 19.9 g of diluted sample into a sterile jar and inoculate with 0.1 mL of $10^7$–$10^8$ suspension of Ps.aeruginosa and mix. At specified time-intervals, transfer 1 mL of inoculated sample to 9 mL of letheen broth and vortex. Plate out serial 1 in 10 dilutions. Pour with tryptone soya agar. Incubate 3 days at 37° C.

EXAMPLE 1

The example describes a method of preparing a poly(2-propenal, 2-propenoic acid) by oxidation of a solid acrolein polymer in air. This poly(2-propenal, 2-propanoic acid) is the preferred method of preparing a starting material for use in the method of the invention. Water (720 mL at ambient temperature, about 20° C.) and acrolein (60 g; freshly distilled, plus hydroquinone added to 0.25% w/w) were placed in an open beaker, within a fume cupboard, and very vigorously stirred, mechanically. Then, 0.2 M aqueous sodium hydroxide (21.4 mL) was added to bring the pH to 10.5–11.0. The solution immediately turned a yellow typical of the hydroquinone anion and within a minute, the colour had disappeared and the clear solution became milky. About 1 minute later, precipitation of a white crystalline, flocculent polymer began, and appeared complete within 15–30 minutes. The precipitate was filtered and washed with water (250 mL), dried at room temperature upon filter papers for 2 days (yield 25 g), then spread as a thin layer in glass petri dishes and heated at 40° C./8 hours. This heating was continued at the following schedules: 50° C./15 hours; 65° C./4 hours; 75° C./18 hours; 84° C./24 hours.

It is envisaged that this method may be scaled-up to include, eg the stepwise addition of acrolein, in a closed vessel, and followed by more rapid drying.

Typically, a solution of the resulting poly(2-propenal, 2-propenoic acid) was prepared by adding 2 g of the subject polymer, with stirring over 15–30 minutes, to a 1% w/w aqueous sodium carbonate solution (100 mL), and then diluted as required. Such solutions were perfectly clear—in contrast to attempted dissolutions, using alternatively, polymer derived from Example 5 of 11686/95; compare Example 5, hereinafter.

EXAMPLE 2

(a) 5 g of poly(2-propenal, 2-propenoic acid) was dissolved in 64 g polyethylene glycol ("PEG") 200 and combined with 31 g of a 0.71% solution of sodium carbonate. A portion of the solution (apparent pH=5.8) was retained at room temperature while the remainder was heated at 60° C. for periods of 12 or 25 days. Samples were diluted with 1% sodium bicarbonate and submitted for biocidal testing at polymer concentrations of 0.125% w/w. Surprisingly, the samples which had undergone "accelerated ageing" showed improved antimicrobial activity, as can be seen by reference to Table 1:

TABLE 1

| Sample, heated | Cfu/ml * (*Pseudomonas aeruginosa*) | | | | |
|---|---|---|---|---|---|
| | 0 min | 10 min | 15 min | 30 min | 60 min |
| 25 days at room temperature | $7.8 \times 10^6$ | $4.1 \times 10^6$ | $6.1 \times 10^5$ | $9.8 \times 10^4$ | <10 |
| 12 days at 60° C. | $7.7 \times 10^6$ | $1.4 \times 10^6$ | $9.8 \times 10^3$ | <10 | <10 |
| 25 days at 60° C. | $1.0 \times 10^7$ | $1.3 \times 10^6$ | $6.6 \times 10^4$ | <10 | <10 |

*Colony forming units/mL (b) 1 g poly(2-propenal, 2-propenoic acid) was dissolved in 200 ml of 0.1% $Na_2CO_3$ and allowed to stand overnight. Sodium lauryl sulphate was introduced at a level of 0.05% and the solution was acidified with HCl to pH 5.9. Portions were stored at both room temperature and 60° C. Biocidal Tests were carried out on 0.125% polymer solutions, with 1% $NaHCO_3$ used as the diluent. The "aged" sample showed a surprising improvement in performance, as can be seen by reference to Table 2:

TABLE 2

| Sample | Cfu/ml * (*Pseudomonas aeruginosa*) | | | |
|---|---|---|---|---|
| | 0 min | 10 min | 15 min | 30 min |
| 20 days at room temperature (RT) | $9.0 \times 10^6$ | $5.1 \times 10^5$ | $6.8 \times 10^2$ | <10 |
| 7 days at 60° C. + 13 days at RT | $9.0 \times 10^6$ | $1.2 \times 10^2$ | <10 | <10 |

* Colony forming units/mL (c) A 5% solution of super-activated polymer was prepared as in example (2a) but replacing PEG200 with PEG1000. A portion of this solution was treated with conc. NaOH to pH 8.1. Samples were heated at 60° C. and submitted for biocidal testing. The sample exposed to more basic conditions unexpectedly gave superior biocidal performance, as can be seen by reference to Table 3:

TABLE 3

| Sample | Cfu/ml * (*Pseudomonas aeruginosa*) | | | | |
|---|---|---|---|---|---|
| | 0 min | 5 min | 10 min | 15 min | 30 min |
| pH 5.8, 12 days 60° C. | $3.8 \times 10^6$ | $2.7 \times 10^6$ | $1.5 \times 10^6$ | $3.3 \times 10^3$ | <10 |
| pH 8.1, 7 days 60° C. | $9.0 \times 10^6$ | — | 10 | <10 | <10 |
| pH 8.1, 17 days 60° C. | $8.3 \times 10^6$ | $3.3 \times 10^5$ | $1.3 \times 10^2$ | <10 | <10 |

* Colony forming units/mL

EXAMPLE 3

(a) 5% solutions of polymers of a range of degrees of super-activation, apparent pH 5.7, were prepared similarly to Example 2(a), but varying the percentage of PEG 200.

Samples were heated at 60° C. and stabilities were monitored over time. Physical stability was considered to have failed with the occurrence of precipitation or gelling. UV measurements were made on a 0.01% polymer concentration in 1% sodium carbonate solution. A decrease of the ratio of absorption at 268 nm: 230 nm is considered synonymous with a decrease in chemical stability. Results are shown in Table 4:

TABLE 4

| Composition | A | B | C | D |
|---|---|---|---|---|
| PEG 200 (% by weight) | 0 | 50 | 64 | 95 |
| Physical Stability | | | | |
| Time | A | B | C | D |
| 4 days 60° C. | Fail | Pass | Pass | Pass |
| 11 days 60° C. | Fail | Fail | Pass | Pass |
| Chemical Stability | Ratio | 260–270 peak absorbance | | |
| | | 228–235 peak absorbance | | |
| Time | A | B | C | D |
| 0 days 60° C. | 1.38 | 1.41 | 1.43 | 1.46 |
| 4 days 60° C. | 0.98 | 1.04 | 1.21 | 1.27 |
| 11 days 60° C. | — | 0.97 | 1.03 | 1.09 |
| 18 days 60° C. | — | 0.89 | 0.92 | 1.04 |
| 25 days 60° C. | — | — | 0.84 | 1.04 |

Both physical and UV spectral results demonstrate the positive effect of PEG on stability; higher PEG content results in greater physical and chemical stabilities.

The following solutions A and B were prepared by dissolving 4 g of poly(2-propenal, 2-propenoic acid) in 196 g 1% sodium bicarbonate and adjusting the pH to 7 (A) and 5.5 (B) with dilute HCl. Solution C was prepared by dissolving 50 g of poly(2-propenal, 2-propenoic acid) in PEG 200 (640 g) at 65°–70° C. Then a solution of 4 g sodium carbonate in water (306 g) was added, the apparent pH being 7, and then 5.5 at the end of the treatment period of 31 days.

All samples were stored at 40° C. At various time intervals samples containing equivalent to 0.125% polymer were submitted for biocidal testing. Results are shown in Table 5:

TABLE 5

| Time(days) at 40° C. | Time for complete kill (minutes) <10 cfu/ml Pseudomonas aeruginosa | | |
|---|---|---|---|
| | Solution A | Solution B | Solution C |
| 0 | 30 | 30 | 30 |
| 7 | 30 | 60 | — |
| 14 | — | — | 10 |
| 31 | 60 | 60 | 10 |

EXAMPLE 4

1 g of poly(2-propenal, 2-propenoic acid) was heated in either a dry or a humid, enclosed chamber, both at 60° C., for 3 days. Solutions of the dry polymer and the humidified polymer, respectively were prepared at 0.125% w/v (with correction for moisture content) and submitted for evaluation by the Biocidal Test:

TABLE 6

| | Cfu/ml * (Pseudomonas aeruginosa) | | | | | |
|---|---|---|---|---|---|---|
| | 0 min | 5 min | 10 min | 15 min | 30 min | 60 min |
| Polymer (dry) | $4.9 \times 10^6$ | — | $7.6 \times 10^5$ | $5.9 \times 10^4$ | $1.2 \times 10^2$ | <10 |
| Polymer (humidified) | $1.1 \times 10^7$ | $6 \times 10^6$ | $3.4 \times 10^3$ | $3.7 \times 10^3$ | <10 | — |

* Colony forming units/mL

The polymers exhibited carbonyl and/or carboxyl absorption in the I.R. between 1700–1730 cm$^{-1}$, carbonyl groups (e.g. with Schiff's reagent) and have $M_w$=ca.10000 and $M_n$=ca.5000; titration shows carboxyl groups ca.5 mole %. These parameters are similar (but not the same) as those of poly(2-propenal, 2-propenoic acid).

EXAMPLE 5

In duplicate experiments, a sample of polymer was prepared and then dissolved in ethane diol, exactly as described in Example 5 of 11686/95. Half of this material was further heated at 80° C. for 24 hours (following which, solubility in aqueous media remained incomplete). The samples were compared for antimicrobial activity, using the standard Biocidal Test. Both of the samples treated by heating, ie. super-activation showed a clear enhancement of antimicrobial activity, as shown in Table 7:

TABLE 7

| Treatment of solution | Cfu/ml * (Pseudomonas aeruginosa) | | | | |
|---|---|---|---|---|---|
| | Initial Count | 5 min | 10 min | 15 min | 30 min |
| (1) None | $4.6 \times 10^6$ | $5.7 \times 10^5$ | $2.9 \times 10^2$ | <10 | <10 |
| (2) None | $4.6 \times 10^6$ | $4.2 \times 10^5$ | $1.5 \times 10^2$ | 10 | <10 |
| (1) 24 hours 80° C. | $4.6 \times 10^6$ | $3.7 \times 10^6$ | <10 | <10 | <10 |
| (2) 24 hours 80° C. | $4.6 \times 10^6$ | $8.0 \times 10^5$ | <10 | <10 | <10 |

* Colony forming units/mL

EXAMPLE 6

50 g of poly(2-propenal, 2-propenoic acid) was dissolved in PEG 200 (640 g) at 65–70° C. Then, an aqueous solution of sodium carbonate (4 g) in water (306 g) was added. The sample was divided and either stood at room temperature or heated at 80° C. for 24 hours. The acrolein content of the solution was determined over time, by reverse phase HPLC and results are shown in Table 8:

TABLE 8

| | Acrolein Content (ppm) | |
|---|---|---|
| Days stored at 20° C. | Super-Activated | Not Super-Activated |
| 0 | 274 | 144 |
| 7 | — | 126 |
| 16 | 34 | 103 |
| 30 | 13 | 80 |

EXAMPLE 7

Solutions of poly(2-propenal, 2-propenoic acid) were prepared as in Example 6 and treated at temperatures of 40, 60, 80, 100 and 115° C. for varying time periods. Samples were Subjected to the standard Biocidal Test to confirm the increased kill rate and results are shown in Table 9.

TABLE 9

| Super-activation Temperature (° C.) | Optimum Time Range (Hours) | Total Kill Time (minutes) |
|---|---|---|
| Room Temperature | >1400 | <10 |
| 40 | 1400 | <10 |
| 60 | 120–170 | <10 |
| 80 | 16–24 | <10 |
| 100 | 4–7 | <10 |
| 115 | 1–3 | <10 |

The amount of time required for super-activation is seen to be inversely proportional to temperature. All solutions of polymers derived from the super-activation process were completely miscible, in all proportions, with aqueous solvents.

EXAMPLE 8

(a) 540 g of poly(2-propenal, 2-propenoic acid) was dissolved in 2304 g PEG200 at 65° C., prior to mixing with 43.2 g of sodium carbonate in 712 g of water. Then, the solution was heated to 100° C. for 4 hours, and 36 g sodium lauryl sulphate, 7 g ECOTERIC T20 (nonionic detergent) and 2 g lemon fragrance were added. The formulation, pH6, was diluted 1:30 with hard water and challenged against

*Staphylococcus aureus* (a gram-positive bacterium, of particular significance regarding infections in hospitals), and Salmonella choleraesuis (a gram-negative bacterium, of particular significance regarding infections in food preparation areas), respectively using the Association of Agricultural Chemists Official Methods of Analysis (1995) 991.47, 991.48, (Hard Surface Carrier Test Method). Results are shown in Table 10:

TABLE 10

| Micro-organism | Positive Tubes | |
| --- | --- | --- |
| S aureus | 2/60 | Pass |
| S. choleraesuis | 1/60 | Pass |

Adjustment of this formulation to higher $pH^s$, increases the antimicrobial activity, as monitored by the Biocidal Test. Results are shown in Tables 11(a) and 11(b):

TABLE 11(a)

Activity against Staphylococcus aureus
Initial Count, $3 \times 10^6$ cfu/ml; polymer 350 ppm.

| pH | 10 minutes cfu/ml | 20 minutes cfu/ml | 30 minutes cfu/ml | 45 minutes cfu/ml | 60 minutes cfu/ml |
| --- | --- | --- | --- | --- | --- |
| 5.6 | $2.8 \times 10^5$ | $4.4 \times 10^4$ | $2.3 \times 10^3$ | 20 | <10 |
| 7.2 | $2.7 \times 10^3$ | <10 | <10 | <10 | <10 |
| 8.9 | $3.2 \times 10^3$ | <10 | <10 | <10 | <10 |
| 10.5 | $1.1 \times 10^2$ | <10 | <10 | <10 | <10 |

TABLE 11(b)

Activity against Pseudomonas aeruginosa
Initial Count, $3.7 \times 10^6$ cfu/ml; polymer 350 ppm.

| pH | 10 minutes cfu/ml | 20 minutes cfu/ml | 30 minutes cfu/ml | 45 minutes cfu/ml | 60 minutes cfu/ml |
| --- | --- | --- | --- | --- | --- |
| 5.6 | $2.9 \times 10^5$ | $8.6 \times 10^4$ | $6.2 \times 10^2$ | 40 | <10 |
| 7.2 | $5.8 \times 10^5$ | $9.1 \times 10^4$ | $4.3 \times 10^3$ | <10 | <10 |
| 8.9 | $9.5 \times 10^5$ | $8.2 \times 10^4$ | $4.6 \times 10^2$ | <10 | <10 |
| 10.5 | $4.5 \times 10^2$ | $3.0 \times 10^3$ | <10 | <10 | <10 |

(b) 1200 g of poly(2-propenal, 2-propenoic acid) was dissolved in 7680 g of PEG200 at 60° C. and then 96 g $Na_2CO_3$ in 3024 g water was added. The solution was heated at 100° C. for 6 hours.

The formulation was added to the basin of an induced draft cooling tower, to a concentration of 300 ppm (30 ppm polymer) 3 times/week. Dosing was carried out at evening to allow contact times of 8–12 hours before operation recommenced; residual concentration was expected to be halved every 3–6 hours of operation. Recirculation water had on average, temperature 27° C., pH 8.5, conductivity 3000 uS. Microbial counts were determined and compared to an adjacent, identical, tower which was dosed with a biodispersant, daily. Results are shown in Table 12:

TABLE 12

| | Cfu/mL * | |
| --- | --- | --- |
| Treatment Time (days) | Treated Tower | Control Tower |
| 1 | $2.4 \times 10^3$ | $1.1 \times 10^7$ |
| 2 | $2.0 \times 10^3$ | $1 \times 10^6$ |
| 3 | $3.3 \times 10^3$ | — |

TABLE 12-continued

| | Cfu/mL * | |
| --- | --- | --- |
| Treatment Time (days) | Treated Tower | Control Tower |
| 4 | $2.5 \times 10^3$ | — |
| 14 | $6.1 \times 10^4$ | $2.6 \times 10^6$ |
| 15 | $5.1 \times 10^4$ | $1.1 \times 10^6$ |
| 16 | $5.1 \times 10^4$ | $4.9 \times 10^6$ |

* Colony forming units/mL

The data indicate the treatment programme maintained the microbial counts within the guidelines of AS/NZ standard 3666.3(Int):1998 and below that in the adjacent tower, containing biodispersant (which was found to be unusually inadequate during the demanding conditions of the very hot, summer period of the test).

Modifications and variation such as would be apparent to the skilled addressee are considered to fall within the scope of the present invention.

What is claimed is:

1. A method for improving the antimicrobial activity of a polymer derived from acrolein monomer wherein the polymer has been oxidized in air to form an oxidized acrolein polymer comprising carboxyl groups, said method comprising:
   providing a solution of the oxidized acrolein polymer comprising carboxyl groups in a mixture containing water and a solvent comprising an alcohol selected from the group consisting of polyols, polyethylene glycols and alkanols; and
   heating the solution at a temperature in the range of from 40 to 150° C. for a period sufficient to improve the antimicrobial activity of the acrolein polymer.

2. A method according to claim 1 wherein said oxidized polymer comprising carboxyl groups is formed by a method of heating a solid acrolein polymer in air at an elevated temperature to form carboxyl groups.

3. A method according to claim 2 wherein said oxidized acrolein polymer comprising carboxyl groups has been formed by heating in air at a temperature between 80° C. and 100° C.

4. A method according to claim 2 wherein the oxidized acrolein polymer comprising carboxyl groups has been formed by heating in air at a temperature of about 85° C.

5. A method according to claim 1 wherein the pH of the solution is in the range of from 7 to 9.

6. A method according to claim 1 wherein the pH of the solution is about 8.

7. A method according to claim 2 wherein the solution includes an alkali selected from an alkali hydroxide, alkali carbonate and mixtures thereof.

8. A method according to claim 7 wherein the alkali is sodium hydroxide, sodium carbonate or mixture thereof.

9. A method according to claim 1, characterised in that the solution is heated in the range of 40 to 115° C.

10. A method according to claim 1, characterised in that the solution is heated in the range of 70–115° C.

11. A method according to claim 9 wherein the solution is heated to about 100° C.

12. A method according to claim 1, characterised in that the solution is heated for a period of between 1 to 1,400 hours, thereby increasing antimicrobial activity of the polymers.

13. A method according to claim 1, characterised in that the solution is heated for a period in the range of from 4 to 60 hours.

14. A method according to claim 11, characterized in that the hydroxylic solvent is polyethylene glycol and is present in the solution in an amount of between 50 and 99% by weight of the solution.

15. A method according to claim 14, characterized in that polyethylene glycol is present in the solution in an amount of between 64 and 95% by weight of the solution.

16. A method according to claim 1, characterized by the addition of base or alkali to the polymers before and/or during heating, thereby enhancing the antimicrobial activity of the polymers.

17. A method according to claim 1, characterised in that the release of free acrolein monomer by the acrolein polymer is reduced.

18. A method according to claim 1 further comprising the step of using the resulting solution for preparation of an antimicrobial formulation.

19. A method according to claim 1 further comprising using the resulting solution for preparation of a preservative, disinfectant or antiseptic.

* * * * *